United States Patent [19]

Ganslaw et al.

[11] 4,090,013
[45] May 16, 1978

[54] ABSORBENT COMPOSITION OF MATTER

[75] Inventors: Stuart H. Ganslaw, Piscataway; Howard G. Katz, East Windsor, both of N.J.

[73] Assignee: National Starch and Chemical Corp., Bridgewater, N.J.

[21] Appl. No.: 556,291

[22] Filed: Mar. 7, 1975

[51] Int. Cl.² ................... C08F 8/42; C08L 3/04; C08L 5/00
[52] U.S. Cl. ................... 526/15; 128/284; 128/296; 252/431 C; 252/431 P; 252/431 R; 260/79.3 MU; 260/79.7; 260/113; 260/117; 260/119; 260/DIG. 47; 424/65; 424/66; 424/68; 424/78; 424/81; 526/16; 526/47.3; 526/47.6; 526/81; 526/86; 526/240; 526/317; 536/3; 536/101; 536/102; 536/121

[58] Field of Search .......... 260/80 L, 78.5 L, 80.3 R, 260/DIG. 31, 79.3 MU, 79.7, 113, 117, 119; 450/607.5; 526/16, 15; 536/3, 101, 102, 121; 252/431 R, 431 C, 431 P

[56] References Cited

U.S. PATENT DOCUMENTS

| 2,103,153 | 12/1937 | Dunham | 260/9 |
| 2,861,045 | 11/1958 | Langer | 252/430 |
| 3,081,291 | 3/1963 | Richmond | 260/94.9 |
| 3,563,978 | 2/1971 | Ochs | 260/232 |
| 3,779,952 | 12/1973 | Leonard | 260/2.5 R |
| 3,886,125 | 5/1975 | Chromecer | 260/78.36 UA |

Primary Examiner—Stanford M. Levin
Attorney, Agent, or Firm—James & Franklin

[57] ABSTRACT

A dry, solid, water-swellable, water-insoluble absorbent composition of matter comprises an ionic complex of a water-soluble anionic poly-electrolyte and a polyvalent metal cation. The composition is characterized by an ability to uncomplex at an elevated pH and recomplex at a lower pH.

42 Claims, No Drawings

ABSORBENT COMPOSITION OF MATTER

BACKGROUND ON THE INVENTION

The present invention relates in general to a dry, solid, water-swellable, water-insoluble absorbent composition of matter, and more particularly to such a composition of matter which provides a gelatinous agglomerate of liquid - swollen particulate members in the presence of a quantity of body exudate, is capable of absorbing at least 15 times its weight in body exudate, and is capable of retaining the absorbed exudate when exposed to pressure sufficient to deform the agglomerate.

As evidenced by such recent patents as U.S. Pat. Nos. 3,628,534, 3,699,103, and 3,670,731, there has been a high degree of activity in the area of water-insoluble particulate hydrocolloid absorbent compositions of matter and products using the same, such as absorbent dressings, diapers, catamenial tampons, and the like. Such compounds maintain their particulate character as they imbibe and absorb many times their weight of surrounding liquid, and in doing so swell. The compounds are capable of absorbing at least 15 times their weight of water, urine and other body exudates. In doing so, each individual absorbent particle swells or enlarges several hundred percent times its individual parameter without destruction of its initial particulate integrity. As the water-insoluble compound accepts liquid, it substantially immobilizes the liquid therein, and the resulting particulate liquid-swollen structure is gelatinous.

The mass of swollen particulate water-insoluble particles defines an aciniform structure since each individual absorbent particle is a greatly enlarged particle, having become liquid-swollen or grape-like or acinus in form due to the water, urine or other liquid it has absorbed. The individual swollen particles are tacky and hence form a clustered mass of liquid-swollen particles. The particles remain in this aciniform state even in the presence of liquid in excess of their ability to absorb.

The liquid-swollen particles bind their absorbed water tightly, but upon drying the particles are dehydrated and return more or less to their original size. At this time they can operate more or less as before to absorb and bind liquids.

The water-insoluble particles described above are generally formed through the polymerization of one or more monomers, which if homopolymerized would form a water-soluble polymer, with a monomer which covalently crosslinks the molecule and introduces a limited water-insolubility. In general the degree of crosslinking is contained so that the polymer network of the hydrocolloid is not soluble in water, urine and the like, yet remains flexible and swells as water and other liquid is absorbed within its structure. As the hydrocolloid swells, it maintains the approximate shape and geometry it had before contact with liquid, but the dimensions are greatly enlarged to provide for the binding of the liquid absorbed therein.

Such water-insoluble hydrocolloid absorbent compositions of matter represent an advance over the prior art watersoluble hydrocolloid materials which merely increase the viscosity of (i.e. thickens) the liquid exposed thereto. Such soluble hydrocolloids serve only to increase the viscosity of the liquid and, in the presence of an added liquid excess, lose their power to retain the viscosity they had previously achieved.

Nonetheless, even the water-insoluble hydrocolloid absorbent compositions described above have not proven to be entirely satisfactory, especially from the point of view of the manufacturer. The prior art water-insoluble absorbent compositions are typically formed by the incorporation into a monomer mixture to be polymerized of a known covalently crosslinking monomeric agent, typically a non-conjugated divinyl compound such as methylene bis acrylamide. As such covalent crosslinking agents actually entered into the formation of the linear polymeric backbone of the absorbent composition, post-polymerization addition of the crosslinking agent (i.e., addition of the cross-linking agent after formation of the linear polymer backbone) could not be utilized, and the manufacturer thus required full polymerization facilities rather than the more limited facilities required for merely adding a crosslinking gent to a prepolymerized mixture and effecting the desired crosslinking. Another disadvantage of the known water-insoluble hydrocolloid compositions is that the composition, once formed, had to be applied to the substrate (for example, the backing of an absorbent dressing) by techniques for handling solids rather than the simpler techniques available for handling liquids.

Accordingly, it is an object of the present invention to provide a water-insoluble absorbent composition of matter in which the water-soluble polymeric backbone may be rendered water-insoluble either during or after polymerization.

It is also an object to provide such a composition in which the various ingredients thereof may be applied as a solution to a substrate and easily converted in situ to the water-insoluble composition.

SUMMARY OF THE INVENTION

It has now been found that the above and related objects of the present invention are attained in a dry, solid, water-swellable, water-insoluble absorbent composition of matter comprising an ionic complex of a water-soluble anionic polyelectrolyte and a polyvalent metal cation having a valence of at least 3, the cation being present in the amount of 0.01–5.0 milliequivalents per gram of poly-electrolyte. The composition provides a gelatinous agglomerate of liquid-swollen particulate members in the presence of a quantity of body exudate, is capable of absorbing at least about fifteen times its weight in body exudate, is capable of retaining absorbed exudate when exposed to pressure sufficient to deform the agglomerate, and is capable of uncomplexing at an elevated pH and recomplexing at a lower pH. The latter feature enables its application to a substrate by conventional fluid application techniques.

The poly-electrolyte generally contains anionic groups, such as carboxylate, sulfonate, sulfate and phosphate groups, and mixtures thereof. Up to 95%, and preferably 40–85%, of such groups may be neutralized to enhance absorbency of the composition. Preferably the poly-electrolyte is a synthetic polymer, polyacrylic acid being especially preferred.

The cation is a metal, preferably aluminum, iron, chromium, zirconium, titanium, or mixtures thereof, with aluminum being especially preferred. The cation is optimally present in the amount of 0.1–1.0 milliequivalents per gram of poly-electrolyte.

In a preferred composition the poly-electrolyte is polyacrylic acid having 40–85% of its carboxylate groups neutralized, and the cation is aluminum and is present in the amount of 0.1–1.0 milliequivalents per gram of poly-electrolyte.

DETAILED DESCRIPTION OF THE PREFERRED EMBODIMENTS

The dry, solid, water-swellable, water-insoluble absorbent composition of matter comprises an ionic complex of two essential ingredients: a water-soluble anionic polyelectrolyte, and a polyvalent metal cation. The poly-electrolyte is a natural or synthetic polymer characterized by substantial water-solubility in an aqueous medium of some relatively neutral pH (somewhere from 2.0 to 8.5 pH) and by the presence of anionic groups (preferably carboxyl, sulfonate, sulfate or phosphate anionic groups). The preferred natural polymers are the anionic derivatives of starch or cellulose, and the preferred synthetic polymers are the carboxylic acid homopolymers or copolymers containing at least 20 mole percent carboxylic acid units, e.g., polyacrylic acid.

Exemplary of the carboxylic acid-containing polyelectrolytes are the synthetic copolymers of ethylenically unsaturated monomers with mono-ethylenically unsaturated carboxylic acids or their partially neutralized salts. Examples of the preferred $\alpha,\beta$-mono-unsaturated carboxylic acids include acrylic acid, methacrylic acid, maleic acid, maleic anhydride, itaconic acid, itaconic anhydride, fumaric acid, half esters or half amides of maleic, fumaric and itaconic acid, crotonic acid, etc. Examples of the preferred $\alpha,\beta$-ethylenically unsaturated monomers include acrylamide or methacrylamide and their N and N, N dialkyl derivatives containing 1–18 carbon alkyl groups, alkyl acrylates and methacrylates containing 1–18 carbon alkyl groups, vinyl esters, vinyl aromatic compounds, dienes, etc.

Homopolymers of monoethylenically unsaturated carboxylic acids or mixtures of these monomers may also be used. Examples include acrylic and methacrylic acid homopolymers and acrylic acid/methacrylic acid copolymers.

Examplary of the sulfonic acid-containing polyelectrolytes are the homopolymers of monoethylenically unsaturated sulfonic acids (or salts thereof) and copolymers thereof with the aforementioned ethylenically unsaturated monomers. Suitable sulfonate-containing monomers include aromatic sulfonic acids (such as styrene sulfonic acids, 2-vinyl-3-bromobenzenesulfonic acid, 2-vinyl-4-ethylbenzenesulfonic acid, 2-allylbenzene sulfonic acid, vinylphenylmethane-sulfonic acid and 1-sulfo-3-vinylphenylmethane sulfonic acid), heterocyclic sulfonic acids (such as 2-sulfo-4-vinylfurane and 2-sulfo-5-allylfurane), aliphatic sulfonic acids (such as ethylenesulfonic acid and 1-phenylethylene sulfonic acid), sulfonic acids containing more than a single acid radical (such as $\alpha$-sulfoacrylic acid and $\alpha$-sulfoethylenesulfonic acid), and sulfonic acid derivatives hydrolizables to the acid form (such as alkenyl sulfonic acid compounds and sulfoalkylacrylate compounds).

Exemplary of the sulfate-containing polyelectrolytes are those formed by reacting homopolymers and copolymers containing hydroxyl groups or residual polymer unsaturation with sulfur trioxide or sulfuric acid; for example, sulfated polyvinyl alcohol, sulfated hydroxyethyl acrylate, sulfated hydroxypropyl methacrylate. Exemplary of the phosphate-containing poly-electrolytes are the homopolymers and copolymers of ethylenically unsaturated monomers containing a phosphoric acid moiety, such as methacryloxy ethyl phosphate.

Exemplary of the poly-electrolytes formed of natural polymers and their derivatives are the carboxylated, sulfonated, sulfated, and phosphated derivatives of cellulose and starch, such as carboxymethyl cellulose and carboxymethyl starch. Naturally occurring anionic poly-electrolytes such as alginates, carrageenen, proteins (such as gelatin, casein, and soya protein), gum arabic, algin, agar, gum ghatti also have utility.

The polymers may be prepared by conventional polymerization techniques, such as solution, emulsion, suspension, and precipitation polymerization techniques. While the polymers are preferably prepared using a free radical polymerization mechanism, other polymerization mechanisms, including anionic and cationic mechanisms, may be used.

The poly-electrolyte generally has a molecular weight of from 10,000 to 10,000,000. It has been found that the absorbency of the composition is improved when the poly-electrolyte is at higher molecular weight levels within the specified range. Accordingly, various di-functional monomers such as allyl methacrylate may be used to chain extend the poly-electrolyte prior to exposure to the cation. The amount of chain extender used must, of course, not render the poly-electrolyte insoluble in aqueous media. The increased chain length of the poly-electrolyte permits lower cation levels to be employed as there are fewer polymer chains to be complexed.

It has further been found that the absorbency of the composition is improved when the poly-electrolyte has up to about 95%, preferably 40—85% of its anionic groups neutralized with a suitable base such as an alkali metal hydroxide, a primary, secondary or teritary amine, etc. The neutralization acts to uncoil and straighten out the polymer chains in aqueous fluids so that the final complex is more swellable in the presence of such fluids.

The polyvalent metal cation complexes the above described poly-electrolyte to render the overall polymer composite substantially insoluble yet highly swellable. The cations have a valence of at least three and are cations of metals belonging to the following groups of the periodic table: IIIB, IVB, VB, VIB, VIIB, VIII, IIIA, IVA, VA, VIA. The preferred metals are aluminum, zirconium, chromium, titanium and iron, and to a lesser degree antimony and bismuth. Aluminum is an especially preferred metal.

The metal compound can be added prior to, during polymerization or post-added to a polymeric poly-electrolyte solution, the only restraint being that the metal compound be at least ionizable or soluble in the polymer system. The polyvalent metal can be added to the composition by means of a basic, acidic or neutral salt, hydroxide, oxide or other compound or complex which has at least limited solubility in water or an organic solvent in which the poly-electrolyte and/or its constituent monomers are also soluble at the time of cation introduction.

Examples of inorganic salts include chlorides, nitrates, sulfates, borates, bromides, iodines, fluorides, nitrites, perchlorates, phosphates, and sulfides, such as aluminum chloride, aluminum sulfate, ferric sulfate, ferric nitrate, antimony trichloride, bismuth chloride, zirconium chloride, chromic sulfate, and chromic nitrate. Examples of organic salts include salts of carboxylic acids such as carbonates, formates, acetates, butyrates, hexanoates, adipates, citrates, lactates, oxalates, oleates, propionates, salicylates, glycinates, glycollates and tartrates; for example, aluminum formoacetate, basic aluminum acetate, chromic acetate, aluminum citrate, aluminum diformate, aluminum triformate, titanium oxalate, ferric acetate, aluminum octate, ferric oleate, zirconium lactate and zirconium acetate.

The ammonia and amine complexes (and especially those coordinated with ammonia) of these metals are particularly useful. Amine capable of so complexing include morpholine, monoethanol amine, diethylaminoethanol and ethylenediamine. Examples of these amine complexes include ammonium zirconyl carbonate, ammonium zirconyl glycinate, and ammonium zirconium chelate of nitrilotriacetic acid. Polyvalent metal complexes (salts) of organic acids that are capable of solubilization in an alkaline pH range may also be employed. Such anions as acetate, glutamate, formate, carbonate, salicylate, glycollate, octoate, benzoate, gluconate, oxalate and lactate are satisfactory. Polyvalent metal chelates wherein the ligand is a bidentate amino acid, such as glycine or alanine, are particularly useful.

Other organic compounds containing polyvalent metals are also useful; for example, the metal alkoxides, metal alkyls, and acetyl acetonates, such as aluminum isopropoxide, titanium acetyl acetonate, aluminum acetyl acetonate, chromic acetyl acetonate, zirconium ethoxide, chromic isobutoxide and triethyl aluminum.

The cations of one or more of such metals are present in the absorbent composition at a level of 0.01–5.0 milliequivalents of cation per gram of poly-electrolyte, and preferably 0.1–1.0 milliequivalents of cation per gram of poly-electrolyte. Lower cation levels do not render the polymeric composition water-insoluble, while higher cation levels render the polymer composition not only water-insoluble, but also non-swellable.

Lower cation levels within the range are especially effective when the poly-electrolyte is of relatively high molecular weight. Regardless of pH, higher cation levels within the specified range contribute to the permanency of the gel formed by exposure of the dried complex to the fluid to be absorbed; but it is noted that in many applications (e.g., diapers, tampons, etc.) a gel life of only a few hours is required and hence lower cations levels within the specified range may be suitable. In general it has been found that the optimum cation level varies with the ion size of the cation.

As will be recognized by those familiar with the art of complexing, not all of the available ionic linkages of a given polyvalent cation will necessarily be associated with different poly-electrolyte polymeric chains, Especially in the case of the cations such as zirconium, having valence or oxidation states greater than 3, inner salt formation (that is, the attachment of a single cation exclusively to a single polymer chain or to a number of polymer chains less than the valence) will occur to an unspecified degree dependent on the spatial geometries presented by the reagents involved, relative concentrations, etc. Accordingly, the specification herein of the relationship of milliequivalent weights of cation per gram of poly-electrolyte is predicated not on a theoretical basis, but rather on experimental results.

The light-to-moderate complexing of the watersoluble poly-electrolyte renders the composition waterinsoluble, but water-swellable. The dry absorbent composition is rendered, in the presence of a quantity of body exudate or other water-containing material into a gelatinous agglomerate of liquid-swollen particulate members. The composition is capable of absorbing at least 15 times its weight in body exudate, and generally at least 40 times its weight. Furthermore, the composition is capable of retaining the absorbed exudate even when exposed to pressure sufficient to deform the agglomerate, and generally up to pressures of about 2.5 psi.

The absorbent capacity of the composition is independent of its physical dry form, and accordingly the composition may be used as a film, powder, or fiber. It can be utilized as an absorbent of any aqueous fluid mixture such as water, blood or urine, and is useful in conjunction with other materials to form articles of manufacture (such as absorbent dressings, diapers, sanitary napkins, catamenial tampons, cosmetics, absorbent non-woven fabrics, and the like) as well as by itself (as an absorbent body powder, soil additive to maintain moisture, anti-perspirant, seed germination aid, pet litter additive to absorb urine, and the like). The composition may be utilized furthermore in articles of manufacture where water absorbency is not the end in and of itself, but merely a means to the end; for example, the absorbent composition may be an ingredient of tablets designed to dissolve rapidly in water or bodily fluids.

The poly-electrolytes of the present invention must be substantially water-soluble at some pH between 2.0 and 8.5 to utilize the metal complexing and form the desired water-insoluble absorbent complex. However, the reversibility of ionic complexing (as opposed to covalent bonding) is well known in the chemical art and once the pH of the complex is raised above a certain level (i.e., the pH of reversibility), the complex breaks down, yielding again the water-soluble non-absorbent poly-electrolyte. This reversibility of complex formation facilitates easy and economical application of the complex onto a desired substrate by use of conventional fluid application techniques. Prior to application a suitable quantity of a base is added to the complex to cause dissolution thereof into a solution containing the cation and the water-soluble poly-electrolyte thereof, and subsequent to application an acid is added to the solution to cause re-formation of the absorbent complex. In a preferred technique a volatile base (such as ammonium hydroxide) is employed to break the complex so that mere drying of the solution suffices to lower the pH and hence cause re-formation of the absorbent complex without the addition of an acid. The acid strength of the poly-electrolyte acid has a marked effect upon the pH of reversibility. The higher the acid strength (i.e., the lower the pH of dissociation), the lower the pH of reversibility. For example, polyacrylic acid, a weak polymeric acid, reverses its complex at pH 8.5–9.0 where styrene sulfonic acid, a very strong polymeric acid, reverses its complex at a pH of about 3.5–5.0.

The preferred composition is a polyacrylic acid/aluminum cation complex. The aluminum cation is typically added (as aluminum acetate) during precipitation polymerization of the acrylic acid with a free radical catalyst, to provide about 0.3 milliequivalents of aluminum per gram of polymer, according to the following formulation:

| Parts by Weight | Ingredient |
|---|---|
| 73.07 | potassium acrylate |
| 27.74 | acrylic acid |
| 0.19 | allyl methacrylate |
| 1.49 | basic aluminum acetate |

EXAMPLES

The following examples illustrate the efficacy of the present invention. All parts are by weight unless otherwise specified. Example I illustrates preparation or obtaining of the poly-electrolytes, Example II illustrates post-addition of the cations, and Example III illustrates the film swell index of the resultant complexes. Example IV illustrates the technique of adding the cation to the poly-electrolyte during polymerization.

EXAMPLE I

Samples 1-27 of the poly-electrolytes indicated in TABLE I were prepared or obtained as follows: Samples 1 - 10 (preparation of polyacrylic acid in aqueous solution). 2210 grams of water and 400 grams of acrylic acid were charged to a three liter round bottomed flask equipped with agitation, condenser, nitrogen purge and heating bath. The contents were agitated under nitrogen purge while heating to 70° C a solution of 50 grams of water and 0.80 grams of ammonium persulfate was uniformly added in increments over 30 minutes while maintaining 70° C. One hour past the addition, 0.40 grams of ammonium persulfate was added. After a total reaction time of 3.5 hours, the reaction was cooled. The final polymer product had a solids content of 11.5%.

Samples 11-16 (preparation of other polymers in aqueous solution). A total of 100 grams of ingredients in Table I and 1,000 grams of water were added to a three liter flask. Under nitrogen purge the solution was heated to 70° C. A catalyst solution of 30 grams water containing 0.30 grams ammonium persulfate was prepared. After reaching 70° C, 3.0 grams of the catalyst solution were added, and the remainder uniformly added over 2.0 hours. After a total reaction time of 3.0 hours, the resultant polymer solutions were cooled.

AMPS is the tradename of Lubrizol Corp. for 2 acrylamide-2methyl propane sulfonic acid.

Samples 17-23 (use of commercial polymers)

The polymeric ingredients in Table I were obtained from the suppliers indicated below:

Starch sodium sulfate having a degree of substitution (DS) of 1.5 was obtained from National Starch and Chemical Corporation (Sample 17).

LYTRON 810 is the tradename of Monsanto Co. for a styrene/maleic anydride copolymer (Sample 18).

GANTREZ AN 139 is the tradename of GAF Corp. for a methyl vinyl ether/maleic anydride copolymer (Sample 19).

KELZAN is the tradename of Kelco Corp. for a polysaccharide derived from kelp (Sample 20).

Sodium carboxymethyl starch having a DS of 0.2 was obtained from National Starch and Chemical Corporation (Sample 21).

Sodium carboxymethyl cellulose having a DS of .75 was obtained from Hercules, Inc. (tradename: CMC-7H) (Samples 22-23).

Samples 24-27 (preparation of polyacrylic acid in non-aqueous solution). To prepare polyacrylic acid by non-aqueous polymerization, 450 grams of anhydrous methanol, 150 grams of acrylic acid and 0.15 grams of t-butyl peroxypivalate were charged to a three liter flask equipped with agitation, condenser, and heating bath. The contents were agitated while heating to reflux (68° C) and held for 30 minutes. Then a solution of 15 grams anhydrous methanol containing 0.15 grams of t-butyl peroxypivalate was added uniformly in increments over two hours at reflux. After a total reaction time of 3.5 hours the reaction mixture was cooled. The final polymer product was a lacquer with a solids content of 23.7%.

EXAMPLE II

The complexes of the present invention were prepared by post-adding the metal compounds indicated in TABLE I to the corresponding poly-electrolyte samples of Example I, as follows:

A. Post addition of metal out of aqueous solution (Samples 1-23)

The polymers of Samples 1-23 were dissolved or diluted in water to 5% solids and adjusted to a desired percent neutralization (as indicated in TABLE I) with sodium hydroxide. Stock solutions in water were prepared of the various metal salts in TABLE I at 0.2-1.0 percent. While stirring the polymeric solutions, the desired amount of metal ions were added to provide the ratios indicated in TABLE I. The solution either increased in viscosity or gelled. Agitation was continued until the metal salt was uniformly incorporated (5-30 minutes). The solutions were then place in a 60° C forced draft oven for 16-24 hours to effect drying. The remaining dry product was a film.

B. Post addition of metal out of non-aqueous solution (Samples 24-27)

The metal chelates of Table I were added as a 1% solution in anhydrous methanol to the polyacrylic acid of Samples 24-27. These solutions were then dried at 65° C for 30 hours to effect drying. The resultant product was a film.

EXAMPLE III

The complex films of Example II were tested for Film Swell Index, with the results reported in TABLE I, as follows:

A. Testing of complex films for Film Swell Index (Samples 1-24)

A small piece of complex film (.05-.10 grams) from Samples 1-24 was weighed analytically to 4 decimal places. To this film was then added a large excess of synthetic urine (0.9% NaCl aqueous solution) — approximately 30 grams. The film was allowed to soak for a total of 4 hours before removing all excess solvent. The swelled film was then reweighed and the film index was calculated as follows in units of grams of synthetic urine/gram polymer:

$$\text{Film swell index} = \frac{\text{final weight} - \text{dry film weight}}{\text{dry film weight}}$$

B. Testing of complex films for Film Swell Index (Samples 25-27)

A similar procedure to that above was employed, but enough 0.1 N sodium hydroxide was added to effect neutralization of the complex film of Samples 25-27 to 65% of their available acidity.

TABLE I

| Poly-electrolyte Composition (% Neutralized) | Sample # | Polyvalent Metal Compound | Milliequivalents metal per gram of polymer | Film Swell Index |
|---|---|---|---|---|
| Polyacrylic acid (65%) | 1 | Aluminum acetate - basic | 1.42 | 26.7 |

TABLE I-continued

| Poly-electrolyte Composition (% Neutralized) | Sample # | Polyvalent Metal Compound | Milliequivalents metal per gram of polymer | Film Swell Index |
|---|---|---|---|---|
| " | 2 | " | 0.25 | 40.0 |
| " | 3 | " | 0.10 | 66.1 |
| " | 4 | Chromium acetate | 0.25 | 14.7 |
| " | 5 | " | 0.0625 | 15.6 |
| " | 6 | " | 0.0156 | 42.5 |
| " | 7 | Zirconium acetate | 0.25 | 16.0 |
| " | 8 | Ferric chloride | 0.50 | 53.5 |
| " | 9 | Aluminum sulfate | 0.50 | 49.0 |
| " | 10 | Aluminum chloride | 0.50 | 68.0 |
| Poly-methacrylic acid (50%) | 11 | Aluminum acetate | 0.25 | 38.5 |
| 50 acrylic acid/50 acrylamide (65%) | 12 | " | 1.00 | 29.5 |
| 5 acrylic acid/95 acrylamide (75%) | 13 | " | 0.25 | 18.9 |
| 1 acrylic acid/99 acrylamide (65%) | 14 | Zirconium acetate | 0.50 | 66.8 |
| 20 AMPS/80 acrylamide (75%) | 15 | Aluminum acetate | 0.25 | 65.0 |
| 3.65 AMPS/96.35 Acrylamide (65%) | 16 | Aluminum acetate - basic | 1.00 | 39.9 |
| Starch sodium sulfate (DS-1.5) | 17 | Zirconium acetate | 0.50 | 32.4 |
| Lytron 810 (70%) | 18 | Aluminum acetate | 1.00 | 14.5 |
| Gantrez AN-139 (50%) | 19 | " | 0.20 | 87.0 |
| Kelzan (pH6) | 20 | " | 0.20 | 22.0 |
| Sodium carboxy methyl starch (DS-2) | 21 | " | 1.00 | 19.0 |
| Sodium carboxy methyl cellulose (DS-.75) | 22 | Aluminum acetate-basic | 0.25 | 57.6 |
| " | 23 | " | 0.033 | 83.8 |
| Polyacrylic acid | 24 | Titanium acetyl acetonate | 0.50 | 21.9 |
| " | 25 | " | 0.50 | 37.0 |
| " | 26 | Aluminum acetyl acetonate | 0.50 | 21.8 |
| " | 27 | Ferric acetyl acetonate | 0.50 | 18.1 |

EXAMPLE IV

This example illustrates the non-aqueous precipitation polymerization of a partial potassium salt of polyacrylic acid, with the addition during polymerization of basic aluminum acetate to provide an aluminum cation level of 0.317 milliequivalents of aluminum per gram of polymer.

| Addition A | | |
|---|---|---|
| Methanol | 280 | gms. |
| Addition B | | |
| Acrylic acid | 100 | gms. |
| Basic aluminum acetate | 2.00 | gms. |
| Potassium hydroxide | 50.00 | gms. |
| Methanol | 200 | gms. |
| Addition C | | |
| Methanol | 15.00 | gms. |
| t-butyl peroxypivalate | 0.35 | gms. |

Addition "A" was charged to three liter round bottom flask equipped with agitation, condenser, and heating bath. 25% of Addition "B" was added to the flask and the contents heated to reflux (68° C). Addition "C" was added uniformly over 2 hours. After some precipitation was observed, the remainder of Addition "B" was slowly and uniformly added over one hour.

After a total reaction time of three hours, the product was cooled, filtered, washed and dried at 60° C, yielding a white polymer powder. The powdered product was dispersed in synthetic urine at a concentration of 4.0%. The particles remained particulate and absorbed all of the fluid. The particulate gel was placed upon a vacuum filter and no fluid was extracted at a vacuum of 27 inches of mercury, despite deformation of the gel.

Now that the preferred embodiments of the present invention have been described, various modifications and improvements thereon will become readily apparent to those skilled in the art. Accordingly, the spirit and scope of the present invention is to be limited only by the appended claims, and not by the foregoing disclosure.

We claim:

1. A dry, solid, water-swellable, water-insoluble absorbent composition of matter consisting essentially of an ionic complex of
   (a) an anionic polyelectrolyte which is water-soluble in the absence of the cation of (b); and
   (b) a polyvalent metal cation having a valence of at least 3, said cation being present in an amount within the range of 0.1–1.0 milliequivalents per gram of said polyelectrolyte, depending on said polyelectrolyte, sufficient to render said polyelectrolyte both water-insoluble and water-swellable;
   said composition further being defined as providing a gelatinous agglomerate of liquid-swollen particulate members in the presence of a quantity of body exudate, as having a film swell index in synthetic urine of at least 15, as being capable of absorbing at least fifteen times its weight in body exudate, as capable of retaining said absorbed exudate when exposed to pressure sufficient to deform said agglomerate, and as capable of uncomplexing at an elevated pH to form said water-soluble anionic polyelectrolyte and recomplexing at a lower pH.

2. The composition of claim 1 wherein said cation is aluminum.

3. The composition of claim 1 wherein said polyelectrolyte has 40–85% of its carboxylate groups neutralized by an alkali metal hydroxide or a primary, secondary or tertiary amine or a mixture thereof.

4. The composition of claim 1 wherein said polyelectrolyte is polyacrylic acid having 40–85% of its carboxylate groups neutralized.

5. The composition of claim 4 wherein said polyelectrolyte has 40–85% of its anionic groups neutralized by an alkali metal hydroxide or a primary, secondary or tertiary amine or a mixture thereof.

6. The composition of claim 1 wherein said polyelectrolyte contains anionic groups selected from the group consisting of carboxylate, sulfonate, sulfate and phosphate groups, and mixtures thereof.

7. The composition of claim 1 wherein said cation is selected from the group consisting of aluminum, iron, chromium, zirconium, titanium and mixtures thereof.

8. The composition of claim 1 wherein said polyelectrolyte is an anionic starch or cellulose.

9. A dry, solid, water-swellable, water-insoluble absorbent composition of matter consisting essentially of an ionic complex of
  (a) an anionic polyelectrolyte which is water-soluble in the absence of the cation of (b) and has 40–85% of its anionic groups neutralized; and
  (b) a polyvalent metal cation having a valence of at least 3, said cation being present in an amount within the range of 0.01–5.0 milliequivalents per gram of said polyelectrolyte, depending on said polyelectrolyte, sufficient to render said polyelectrolyte both water-insoluble and water-swellable;
  said composition further being defined as providing a gelantinous agglomerate of liquid-swollen particulate members in the presence of a quantity of body exudate, as having a film swell index in synthetic urine of at least 15, as being capable of absorbing at least about fifteen times its weight in body exudate, as capable of retaining said absorbed exudate when exposed to pressure sufficient to deform said agglomerate, and as capable of uncomplexing at an elevated pH to form said water-soluble anionic polyelectrolyte and recomplexing at a lower pH.

10. The composition of claim 9 wherein said polyelectrolyte is polyacrylic acid having 40–85% of its carboxylate groups neutralized.

11. The composition of claim 10 wherein said polyelectrolyte has 40–85% of its carboxylate groups neutralized by an alkali metal hydroxide or a primary, secondary or tertiary amine or a mixture thereof.

12. The composition of claim 9 wherein said polyelectrolyte has 40–85% of its anionic groups neutralized by an alkali metal hydroxide or a primary, secondary or tertiary amine or a mixture thereof.

13. The composition of claim 9 wherein said cation is present in an amount not in excess of 1.0 milliequivalents per gram of polyelectrolyte.

14. The composition of claim 9 wherein said cation is aluminum.

15. The composition of claim 9 wherein said polyelectrolyte contains anionic groups selected from the group consisting of carboxylate, sulfonate, sulfate and phosphate groups, and mixtures thereof.

16. The composition of claim 9 wherein said cation is selected from the group consisting of aluminum, iron, chromium, zirconium, titanium and mixtures thereof.

17. The composition of claim 9 wherein said polyelectrolyte is an anionic starch or cellulose.

18. A dry, solid, water-swellable, water-insoluble absorbent composition of matter consisting essentially of an ionic complex of
  (a) an anionic polyelectrolyte which is water-soluble in the absence of the cation of (b); and
  (b) a polyvalent metal cation having a valence of at least 3, said cation being present in an amount within the range of 0.01–1.42 milliequivalents per gram of said polyelectrolyte, depending on said polyelectrolyte, sufficient to render said polyelectrolyte both water-insoluble and water-swellable;
  said composition further being defined as providing a gelatinous agglomerate of liquid-swollen particulate members in the presence of a quantity of body exudate, as having a film swell index in synthetic urine of at least 15, as being capable of absorbing at least about 15 times its weight in body exudate, as capable of retaining said absorbed exudate when exposed to pressure sufficient to deform said agglomerate, and as capable of uncomplexing at an elevated pH to form said water-soluble anionic polyelectrolyte and recomplexing at a lower pH.

19. The composition of claim 18 wherein said polyelectrolyte contains anionic groups selected from the group consisting of carboxylate, sulfonate, sulfate and phosphate groups, and mixtures thereof.

20. The composition of claim 18 wherein said cation is selected from the group consisting of aluminum, iron, chromium, zirconium, titanium and mixtures thereof.

21. The composition of claim 18 wherein said polyelectrolyte is an anionic starch or cellulose.

22. A dry, solid, water-swellable, water-insoluble absorbent composition of matter consisting essentially of an ionic complex of
  (a) an anionic polyelectrolyte which is water-soluble in the absence of the cation of (b); and
  (b) a polyvalent metal cation of aluminum having a valence of 3, said cation being present in an amount within the range of 0.01–5.0 milliequivalents per gram of said polyelectrolyte, depending on said polyelectrolyte, sufficient to render said polyelectrolyte both water-insoluble and water-swellable;
  said composition further being defined as providing a gelatinous agglomerate of liquid-swollen particulate members in the presence of a quantity of body exudate, as having a film swell index in synthetic urine of at least 15, as being capable of absorbing at least fifteen times its weight in body exudate, as capable of retaining said absorbed exudate when exposed to pressure sufficient to deform said agglomerate, and as capable of uncomplexing at an elevated pH to form said water-soluble anionic polyelectrolyte and recomplexing at a lower pH.

23. The composition of claim 22 wherein said polyelectrolyte is polyacrylic acid having 40–85% of its carboxylate groups neutralized.

24. The composition of claim 23 wherein said polyelectrolyte has 40–85% of its carboxylate groups neutralized by an alkali metal hydroxide or a primary, secondary or tertiary amine or a mixture thereof.

25. The composition of claim 23 wherein said cation is present in an amount not in excess of 1.0 milliequivalents per gram of polyelectrolyte.

26. The composition of claim 23 wherein said cation is present in the amount of 0.1–1.0 milliequivalents per gram of polyelectrolyte.

27. The composition of claim 22 wherein said polyelectrolyte has 40–85% of its anionic groups neutralized by an alkali metal hydroxide or a primary, secondary or tertiary amine or a mixture thereof.

28. The composition of claim 22 wherein said cation is present in an amount not in excess of 1.0 milliequivalents per gram of polyelectrolyte.

29. The composition of claim 22 wherein said cation is present in the amount of 0.1–1.0 milliequivalents per gram of polyelectrolyte.

30. The composition of claim 22 wherein said polyelectrolyte contains anionic groups selected from the group consisting of carboxylate, sulfonate, sulfate and phosphate groups, and mixtures thereof.

31. The composition of claim 22 wherein said polyeletrolyte is an anionic starch or cellulose.

32. A dry, solid, water-swellable, water-insoluble absorbent composition of matter consisting essentially of an ionic complex of
    (a) an anionic polyelectrolyte which is a water-soluble synthetic polymer in the absence of the cation of (b); and
    (b) a polyvalent metal cation having a valence of at least 3, said cation being present in an amount within the range of 0.1–5.0 milliequivalents per gram of said polyelectrolyte, depending on said polyelectrolyte, sufficient to render said polyelectrolyte both water-insoluble and water-swellable;

said composition further being defined as providing a gelatinous agglomerate of liquid-swollen particulate members in the presence of a quantity of body exudate, as having a film swell index in synthetic urine of at least 15, as being capable of absorbing at least 15 times its weight in body exudate, as capable of retaining said absorbed exudate when exposed to pressure sufficient to deform said agglomerate, and as capable of uncomplexing at an elevated pH to form said water-soluble anionic polyelectrolyte and recomplexing at a lower pH.

33. The composition of claim 32 wherein said cation is aluminum.

34. The composition of claim 32 wherein said synthetic polymer is polyacrylic acid.

35. The composition of claim 34 wherein said polyacrylic acid polymer has 40–85% of its carboxylate groups neutralized by an alkali metal hydroxide or a primary, secondary or tertiary amine or a mixture thereof.

36. The composition of claim 32 wherein said cation is selected from the group consisting of aluminum, iron, chromium, zirconium, titanium and mixtures thereof.

37. The composition of claim 32 wherein said synthetic polymer has 40–85% of its anionic groups neutralized.

38. The composition of claim 32 wherein said synthetic polymer has 40–85% of its anionic groups neutralized by an alkali metal hydroxide or a primary, secondary or tertiary amine or a mixture thereof.

39. The composition of claim 32 wherein said cation is present in an amount not in excess of 1.0 milliequivalents per gram of polyelectrolyte.

40. The composition of claim 32 wherein said synthetic polymer is a carboxylic acid homopolymer or copolymer containing at least 20 mole percent carboxylic acid units.

41. The composition of claim 32 wherein said synthetic polymer contains anionic groups selected from the group consisting of carboxylate, sulfonate, sulfate and phosphate groups, and mixtures thereof.

42. The composition of claim 41 wherein said synthetic polymer has up to 95% of its anionic groups neutralized.

* * * * *